(12) United States Patent
Crisostomo Silva et al.

(10) Patent No.: US 12,402,705 B2
(45) Date of Patent: Sep. 2, 2025

(54) HYGIENE KIT

(71) Applicant: Lourenco Crisostomo Silva, Lisbon (PT)

(72) Inventors: Lourenco Crisostomo Silva, Lisbon (PT); Filipe Crisostomo Silva, Lisbon (PT); Daniel Freire Falcão Teles Caramelo, Lisbon (PT); Agostinho Miguel Quitério Garcia Carvalho, Leiria (PT)

(73) Assignee: Lourenco Crisostomo Silva, Lisbon (PT)

( * ) Notice: Subject to any disclaimer, the term of this patent is extended or adjusted under 35 U.S.C. 154(b) by 455 days.

(21) Appl. No.: 17/806,787

(22) Filed: Jun. 14, 2022

(65) Prior Publication Data

US 2022/0304446 A1    Sep. 29, 2022

Related U.S. Application Data

(63) Continuation of application No. PCT/PT2020/050050, filed on Dec. 14, 2020.

(30) Foreign Application Priority Data

Dec. 16, 2019  (PT) .................................... 115990

(51) Int. Cl.
*A45D 24/16*    (2006.01)
*A45D 24/06*    (2006.01)
(Continued)

(52) U.S. Cl.
CPC ............. *A45D 24/16* (2013.01); *A45D 24/06* (2013.01); *A45D 27/22* (2013.01); *A45D 44/18* (2013.01);
(Continued)

(58) Field of Classification Search
CPC ........ A45D 24/16; A45D 24/06; A45D 27/22; A45D 24/18; A46B 5/0041; A46B 15/0059; A46B 15/0079; A46B 15/0095
See application file for complete search history.

(56) References Cited

U.S. PATENT DOCUMENTS 902,796   A       11/1908   Archer et al.
1,398,583 A  *    11/1921   Bovee ................... A45D 24/16
                                                    30/47
(Continued)

FOREIGN PATENT DOCUMENTS

DE    29914169 U1    6/2000
DE    20014388 U1   12/2000
(Continued)

*Primary Examiner* — Nicholas D Lucchesi
(74) *Attorney, Agent, or Firm* — PERKINS COIE LLP; Michael A. Glenn

(57) ABSTRACT

The present invention refers to a hygiene kit, in particular a hygiene kit that provides collapsible manipulation of at least two tools of personal hygiene, such as for example a toothbrush and a comb, whereby the hygiene kit includes a casing with two casing parts configured with the shape of half-shell that can collect the toothbrush part of the two utensils inside thereof, and adapted so that the utensils can be mechanically retained one with the other by connection parts that also provide rotation support for the swiveling movement of the utensils between respective recollected and utility positions, and vice-versa.

13 Claims, 9 Drawing Sheets

(51) Int. Cl.
*A45D 27/22* (2006.01)
*A45D 44/18* (2006.01)
*A46B 5/00* (2006.01)
*A46B 15/00* (2006.01)
*B26B 21/40* (2006.01)
*B26B 21/52* (2006.01)

(52) U.S. Cl.
CPC .......... *A46B 5/0016* (2013.01); *A46B 5/0041* (2013.01); *A46B 15/0059* (2013.01); *A46B 15/0079* (2013.01); *A46B 15/0095* (2013.01); *A46B 2200/1066* (2013.01); *A61K 2800/87* (2013.01); *B26B 21/4062* (2013.01); *B26B 21/521* (2013.01)

(56) References Cited

U.S. PATENT DOCUMENTS

| | | | | |
|---|---|---|---|---|
| 2,399,660 | A * | 5/1946 | Boulicault | A46B 5/0041 206/229 |
| 2,744,278 | A * | 5/1956 | Roth | A46B 5/0033 15/185 |
| 3,296,642 | A * | 1/1967 | Aylott | A45D 40/28 30/155 |
| 3,734,118 | A * | 5/1973 | Howard | A46B 11/0006 401/125 |
| 3,763,869 | A | 10/1973 | Sanders | |
| 4,204,294 | A * | 5/1980 | Halverson | H01R 43/002 7/168 |
| 5,097,852 | A | 3/1992 | Wu | |
| 5,423,427 | A | 6/1995 | Brown | |
| 8,074,319 | B2 | 12/2011 | Huang | |
| 2005/0039284 | A1 | 2/2005 | Paustell | |
| 2006/0064832 | A1 | 3/2006 | Caramico | |
| 2009/0172958 | A1 * | 7/2009 | Prudden, Jr. | B65D 43/162 30/539 |
| 2022/0031039 | A1 * | 2/2022 | Fellows | A46B 15/0059 |

FOREIGN PATENT DOCUMENTS

| | | |
|---|---|---|
| FR | 2604155 A3 | 3/1988 |
| WO | 2005020837 A2 | 3/2005 |
| WO | 2020051434 A1 | 3/2020 |

* cited by examiner

HYGIENE KIT

CROSS-REFERENCES TO RELATED APPLICATIONS

This application is a continuation of copending International Application No. PCT/PT2020/050050, filed Dec. 14, 2020, which is incorporated herein by reference in its entirety, and additionally claims priority from Portuguese Application No. 115990 filed on Dec. 16, 2019, which is incorporated herein by reference in its entirety.

The present invention refers to the field of hygiene tools, in particular toothbrushes and combing brushes or combs, adapted so that can be collapsed for collection of the brush part inside of a casing part.

BACKGROUND OF THE INVENTION

The conventional technology includes several solutions of toothbrushes provided so that can be collapsed between an open position where they can be used, and a closed position where they are collected inside of a box-like part, so that the brush part is protected from exposure to eventual dusts and dirt.

The document U.S. Pat. No. 902,796 discloses a combination of toothbrush and powder recipient that includes a casing part with two half-shell parts and united on a respective first edge in a swivelling connection so that they can be opened and closed relative to the casing part. Said casing part further includes a toothbrush part on a second edge in a swivelling connection, so that can be collapsed to the interior of the casing part or opened up to an operative position where it can be used by a user, holding the casing part as a handle.

The document U.S. Pat. No. 2,744,278 discloses a construction of a foldable toothbrush that includes a casing part and an utensil part of toothbrush connected by means of swivelling connection to an edge region of the casing part so that can be swivelled between an open position, where it can be operated by the user, and a closed position where it is collected inside the casing part.

The document U.S. Pat. No. 3,763,869 discloses a similar construction, in particular a portable toothbrush that includes a casing part and a toothbrush part adapted so that can be swivelled by a swivelling connection between open and closed positions, and vice-versa.

The document U.S. Pat. No. 5,423,427 also discloses a travel dental kit that comprises a plastic rectangular compartment that has a face that can be turned sideways thereby enabling the opening by at least 90 degrees so as to completely expose the interior of the compartment, whereby a plurality of dental care tools is mounted so that can be vertically rotated outside of the compartment. When rotated outwards, said utensils are blocked in such position by the closure of the turntable face of the compartment, whereby the compartment builds a handle for said utensils in the vertical position.

The document WO 2005/020837 A2 discloses a casing that can retain a toothbrush and other teeth cleaning tools inside thereof. In particular, three different tools can be on a common support of swivelling axis, and adapted so that can be rotated to the interior of a casing space, and to the exterior, to an operative position.

The document US 2005/0039284 A1 also discloses a toothbrush disposition with a head member of toothbrush that can be rapidly deployed.

The document U.S. Pat. No. 8,074,319 B2 discloses a foldable toothbrush that includes a casing part presenting a door-like part that can be swivelled open so as to provide access to the interior of the casing and thereby rotating a toothbrush member out of the interior of the casing.

There is therefore the need to provide a hygiene kit com a plurality of hygiene utensils of more ergonomic use and with a simpler construction.

SUMMARY

An embodiment may have a hygiene kit, presenting: a casing comprising a first and a second casing parts configured with a general handle-like, handle grip, or similar format, elongated along a longitudinal direction, and adapted so that can be retained with each other and thereby provide an interior space of the casing, a first and a second utensil of personal hygiene, such as for example a tooth brush or similar, comprising a support part and an operative part, or similar, characterized in that said first and second utensils are provided so that can be operated in respective swivelling axis between open positions where they can be used, and closed positions where they can be collected through opposite sides inside the interior space of the casing, without requiring opening the casing.

The objective of the present invention is to provide a hygiene kit that comprises a casing part and at least two utensils with support parts and functional parts, for example brush-type parts or similar, said hygiene utensils being adapted so that can be operated between closed and open positions, and vice-versa, said hygiene kit being provided with a simpler general construction, with better reliability and ergonomic of use and lower production costs.

The aforementioned objective is solved according to the present invention by means of a hygiene kit according to claim 1.

In particular, the aforementioned objective is solved by means of a hygiene kit that presents a casing consisting in two casing parts adapted so that can be reciprocally retained and also provide swivel support elements for at least two hygiene utensils so that these utensils can be swivelled between a closed position where they are collected in respective collection interior space through casing opening configured laterally in mutually opposing sides of the casing, along the junction of said two casing parts, and an open position where the hygiene utensils extend along directions parallel to said longitudinal casing sides.

An associated objective is to provide a casing part with a simpler construction, and better use ergonomic, as well as providing the possibility of easy replacement of any of the hygiene utensils.

This objective is solving according to the present invention by means of a hygiene kit whereby a casing consists of two parts provided as single pieces that include operation support elements of the hygiene utensils, and the hygiene kit does not include any additional element of support of the swivelling operation of the hygiene utensils, for example of swivel support beam type, as separate element from said casing parts, and the casing parts are adapted so that can be reciprocally retained by means of pressured fitting, without requiring the use of any tool for this purpose.

The hygiene kit can present a third hygiene utensil, whereby also in this case it can be operated between respective closed and open positions, without the need of gears associated with the casing part and hygiene utensil, and with no additional part for this purpose.

BRIEF DESCRIPTION OF THE DRAWINGS

Embodiments of the present invention will be detailed subsequently referring to the appended drawings, in which.

DETAILED DESCRIPTION OF THE INVENTION

Figure 1:
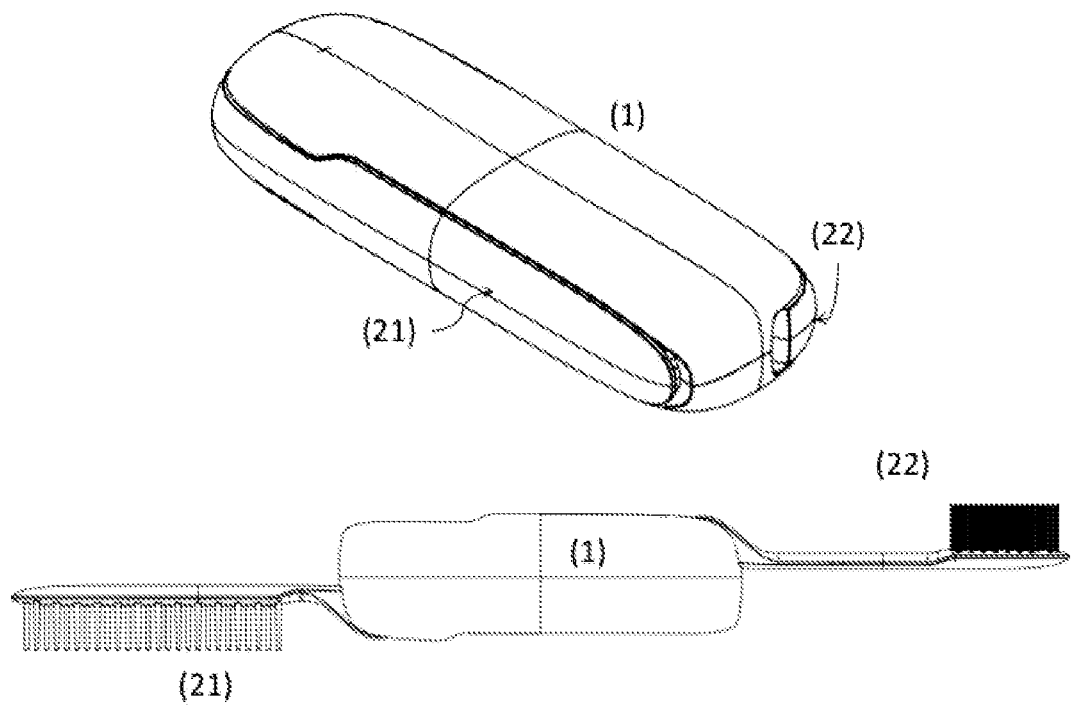
FIG. 1: shows a perspective view (top drawing) and a top view (bottom drawing) of a first embodiment of a hygiene kit according to the present invention, with two utensils (21, 22) in a closed and open position, respectively.
Figure 2:
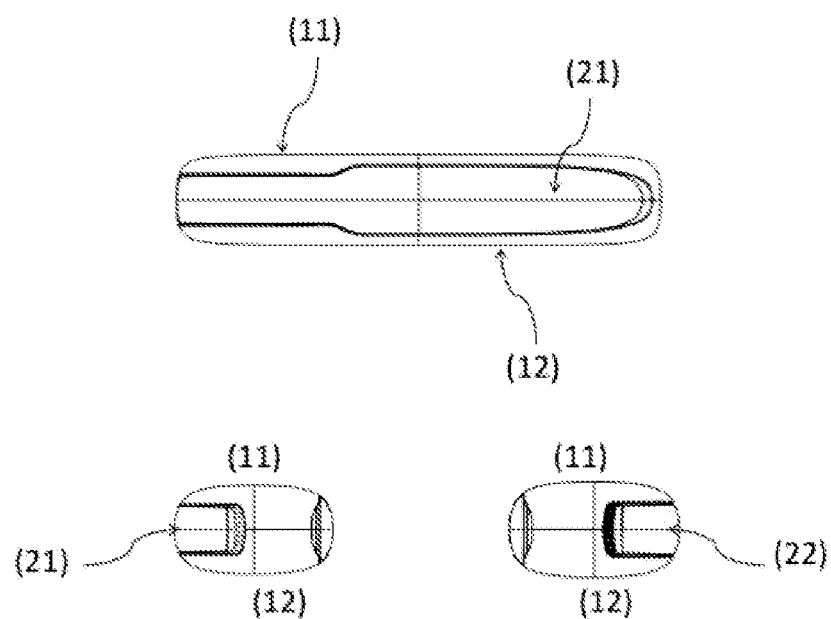
FIG. 2: shows side views (top drawing) and views from each of the tops (bottom) of the embodiment according to FIG. 1, with utensils (21, 22) in a closed position.
Figure 3:
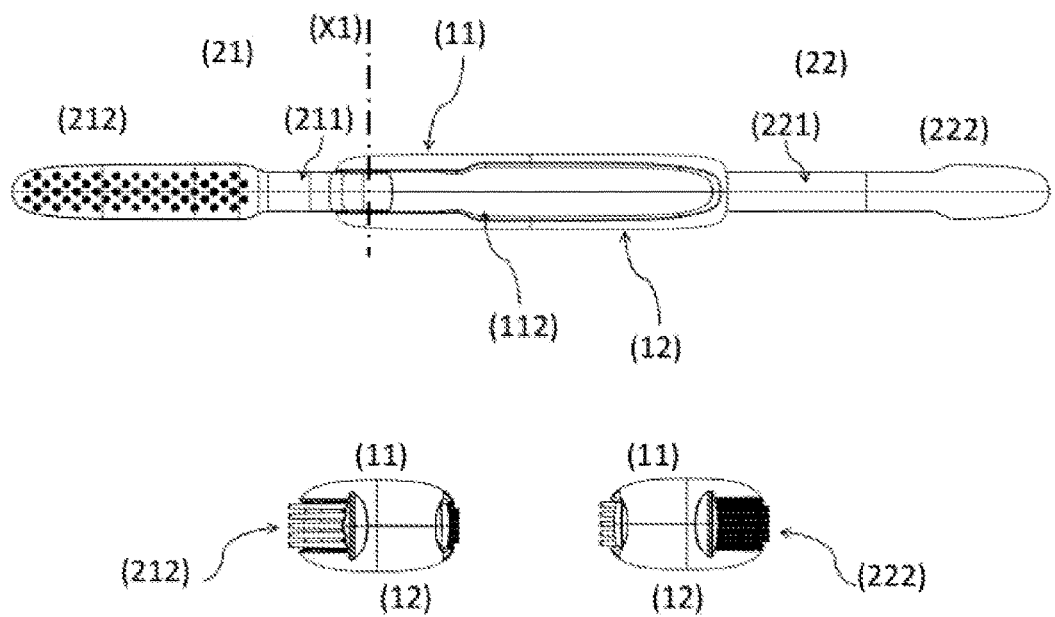
FIG. 3: shows side views (top drawing) and views from each of the top (bottom) of the embodiment according to FIG. 1, with utensils (21, 22) in an open position.

The present invention shall be hereinafter described based upon two embodiments, without the limitation of the scope thereof given that many other embodiments are possible with said scope.

FIGS. 1 to 8 represent different views of a first embodiment of a hygiene kit according to the present invention, presenting a casing (1) and two utensils (21, 22), in particular two hygiene utensils. In the case of this embodiment, it is a combing brush (21) and a toothbrush (22), provided so that can be operated between a closed position, where they can be collected inside of the casing (1), and an open position where they can be used, and vice-versa.

The hygiene kit comprises a casing (1) configured with a general form of handle type, holding support, or similar, and comprising two casing parts (11, 12) each one configured in a half-shell shape and adapted so that can be mechanically retained to each other and thereby provide an interior space.

The casing (1) can present a general shape of rectangular type when seen from the top or from the bottom, with a first longitudinal extension that is bigger than a second transversal extension. The casing (1) can further present a third extension that extends generally orthogonally relative to the plane defined by the first and second extension, and with a dimension that is similar or smaller than the second transversal extension.

Said mechanic retention of the two casing parts (11, 12) can be configured so that can be carried out manually, without requiring the use of a tool, thereby enabling access for replacement of utensils (21, 22).

The first and second utensils (21, 22) comprise a support part (211, 221) adapted so that can be retained in a casing part (1) so that can be swivelled between closed and open positions, and vice-versa, and an operative part (212, 222) adapted so as to provide the required use in each case.

According to an inventive aspect, said first and second utensils (21, 22) are provided so that can be swivelled around respective swivelling axis (X1, X2) and thereby operated between open position where they can be used, and closed position where they can be collected in the interior space through casing openings (111, 112) configured in opposite sides of said casing part (11, 12).

The hygiene kit in this case consists of two casing parts (11, 12) and two utensils (21, 22), not requiring any additional part or component.

A simpler to operate and more ergonomic disposition of hygiene kit is herewith advantageously provided, only requiring manipulation of one opening movement of utensil (21, 22) and without further requiring an opening movement of opening and closing of a casing (1).

Moreover, there is provided a disposition of hygiene kit of reduced construction complexity, and with substantial collection of the operative parts (212, 222), protecting them from exposure to the exterior environment when collected inside of the casing (1).

Said casing openings (111, 112) can be configured with a shape adjusted to the shape of the operative parts (212, 222) of each one of the utensils.

The casing parts (11, 12) can be configured so that, in case of being in the closed position, the exterior surface of the utensils (21, 22) occupies the area delimited by the casing openings (111, 112) and extends in a generally continuous manner with the exterior surface of the casing parts (11, 12).

Said casing openings (111, 112, 121, 122) can be configured with at least one of: different shape and different dimension.

As can be observed in particular in FIGS. 3 to 8, the casing parts (11, 12) present two first casing connections (13) provided in diametrically mutually opposing corner regions thereof, and adapted so that can provide reciprocal pressurized fitting.

In particular, the casing connections (13) are in this case adapted so that can provide an assembly of the casing parts (11, 12) by means of a generally linear movement of fitting engagement thereof.

Figure 5:
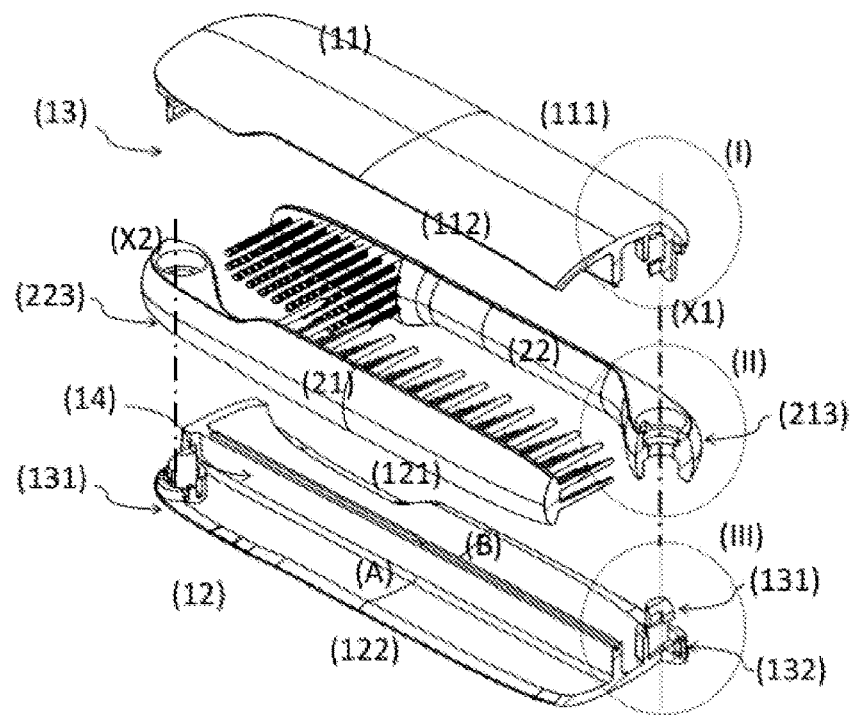
FIG. 5: shows a perspective exploded view of the embodiment according to FIG. 1, with utensils (21, 22) in a closed position.

As can be observed in FIG. 5, the edge region of the support parts (211, 221) of first and second utensils (21, 22) opposite to the operative parts (212, 222), presents a respective retention part (213, 223) that presents a portion configured so that can be rotated between closed and open positions, and that at least partially surrounds a ring-like portion that can operate as female part in a connection to a casing connection (13; 131, 132) provided in the casing part (1).

The first and second casing parts (11, 12) present first casing connections (13; 131, 132) that comprise a reciprocal mechanical retention part (131) and an utensil support part (132) that extends in tubular manner preferentially around the mechanic retention part (131).

Figure 6:
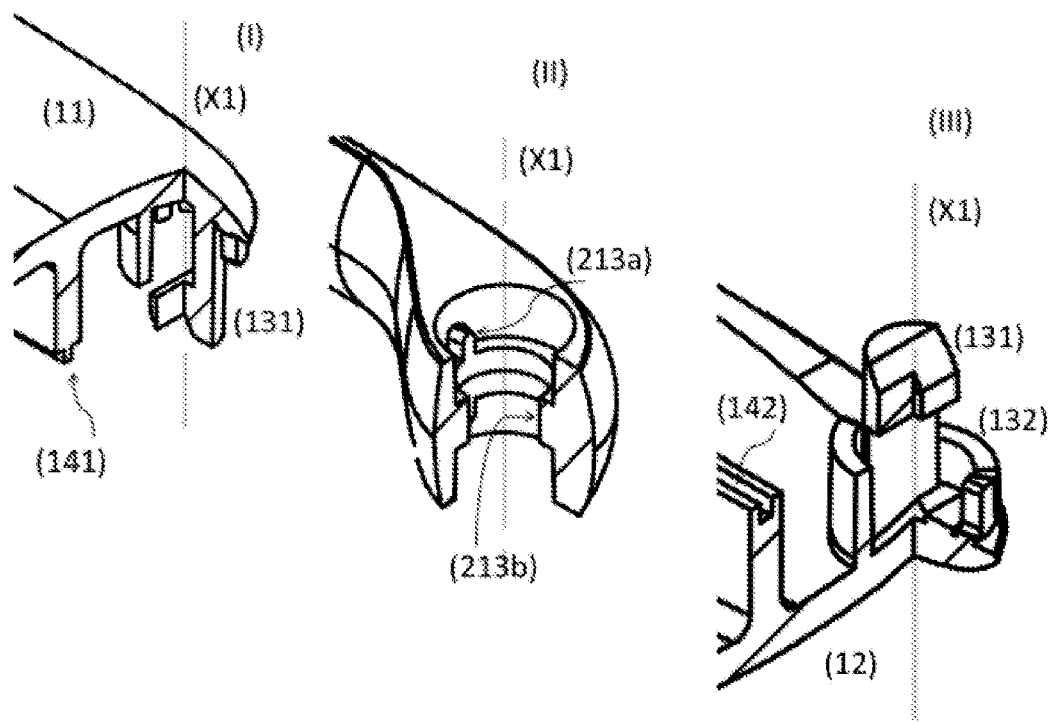
FIG. 6: shows views of the details I, II and III, according to FIG. 5, of the connection portions of the embodiment according to FIG. 1.
Figure 7:
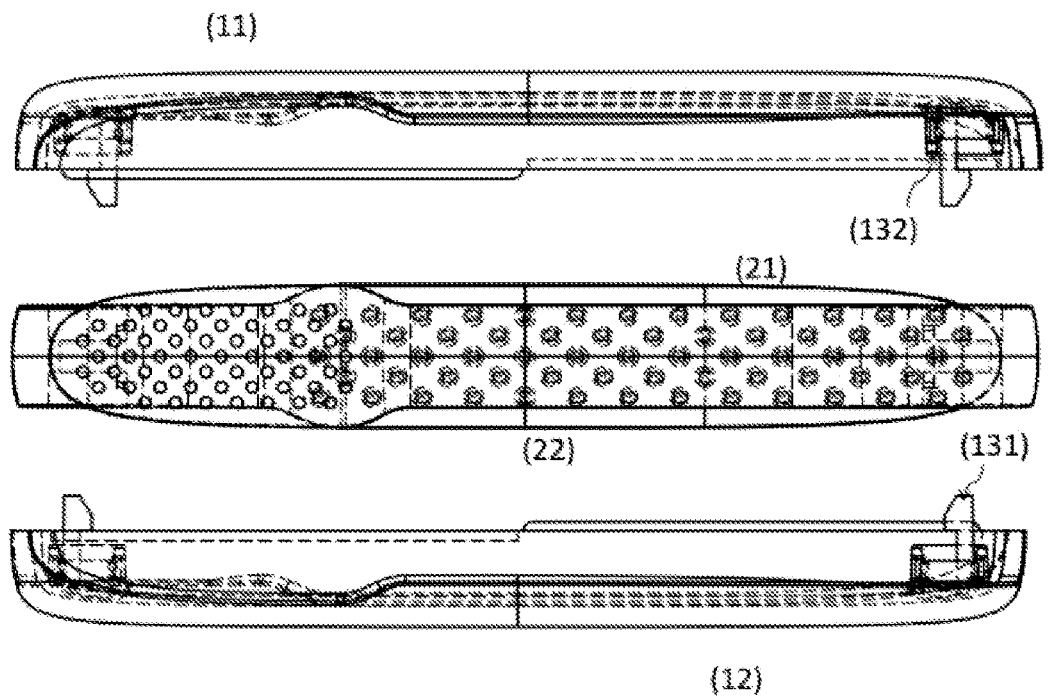
FIG. 7: shows longitudinal side-cut views of the components of the embodiment according to FIG. 1, in a position of unassembled.
Figure 8:
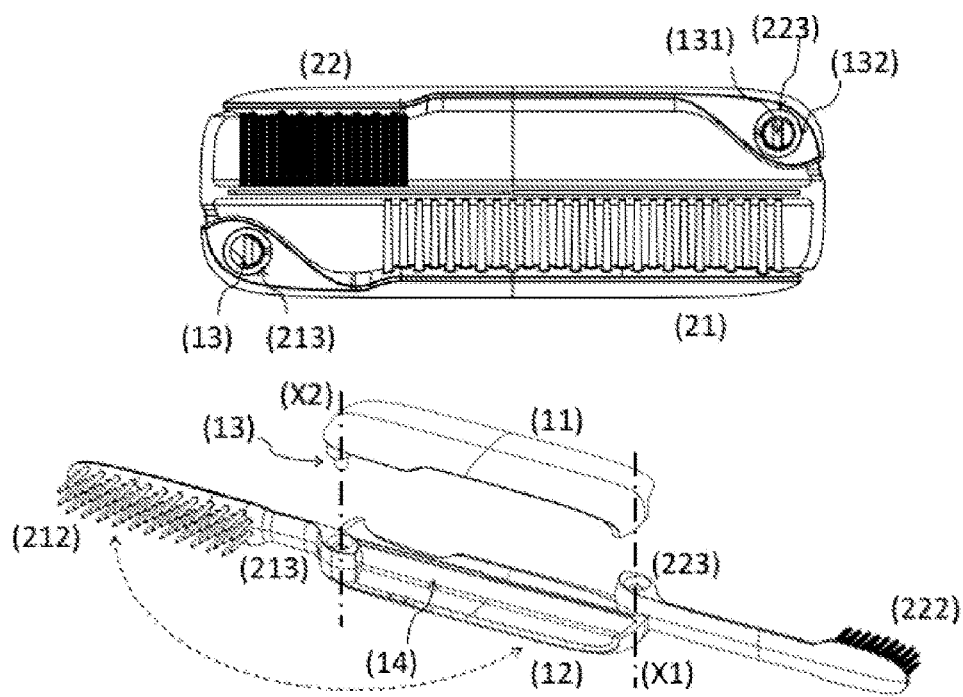
Figure 9:
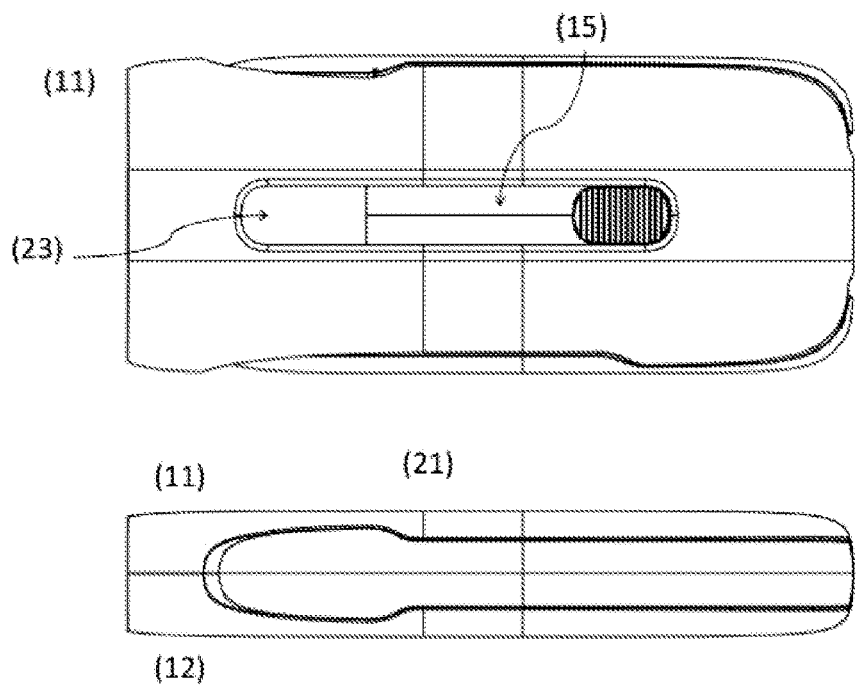
FIG. 9: shows a top view (top drawing) and a side view of a second embodiment of hygiene kit according to the present invention, with utensils (21, 22, 23) in the closed position.
Figure 10:
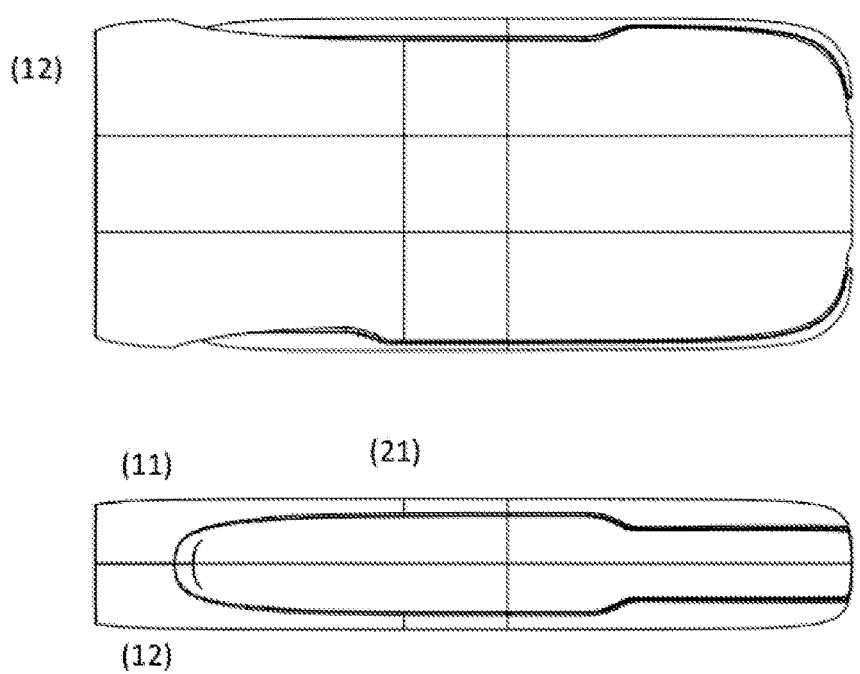
FIG. 10: shows a bottom view (top drawing) and a side view of the embodiment according to FIG. 9, with utensils (21, 22, 23) in the closed position.
Figure 11:
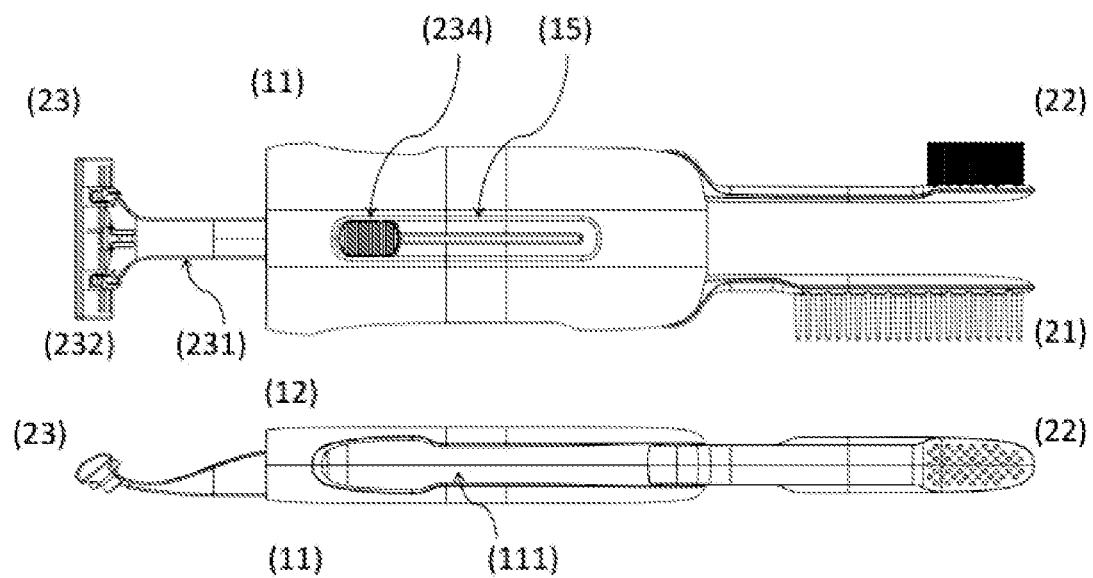
FIG. 11: shows a top view (top drawing) and a side view of the embodiment according to FIG. 9, with utensils (21, 22, 23) in the open position.
Figure 12:
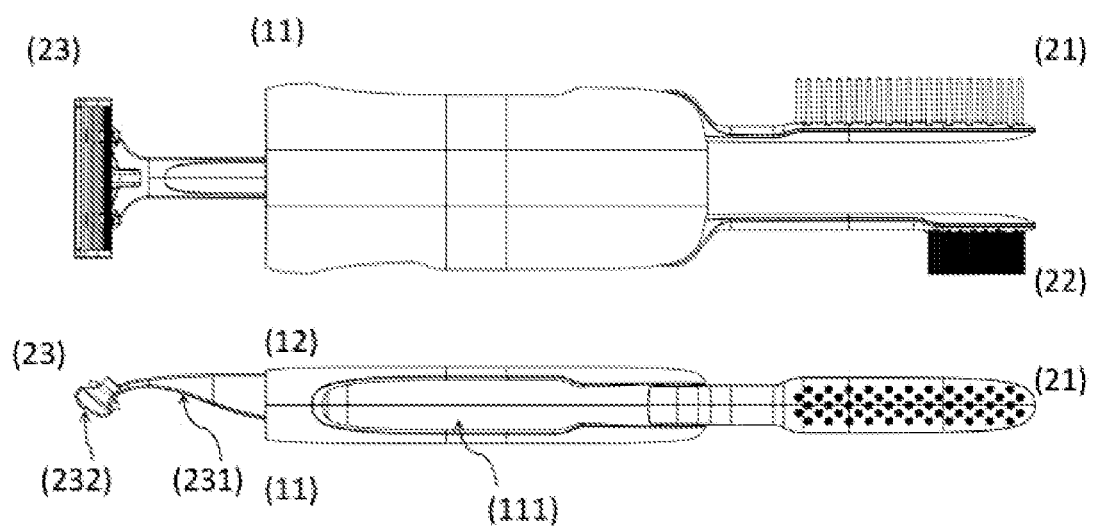
FIG. 12: shows a bottom view (top drawing) and a side view of the embodiment according to FIG. 9, with utensils (21, 22, 23) in the open position.
Figure 13:
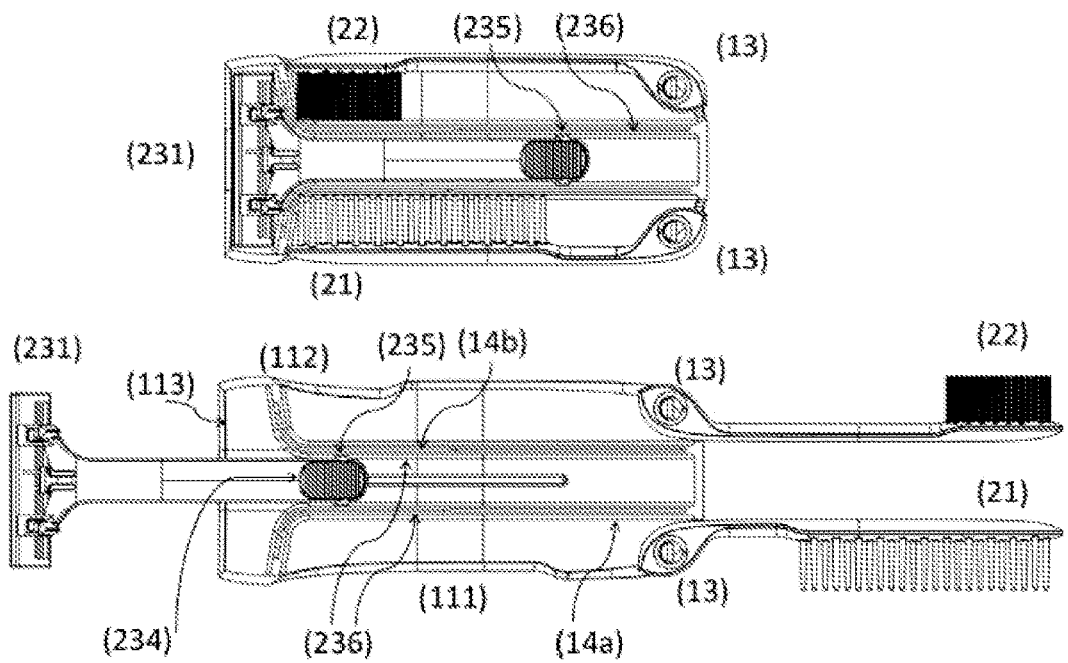
FIG. 13: shows top views of the embodiment according to FIG. 9, without the casing top part, with utensils (21, 22, 23) in closed (top drawing) and open positions.
Figure 14:
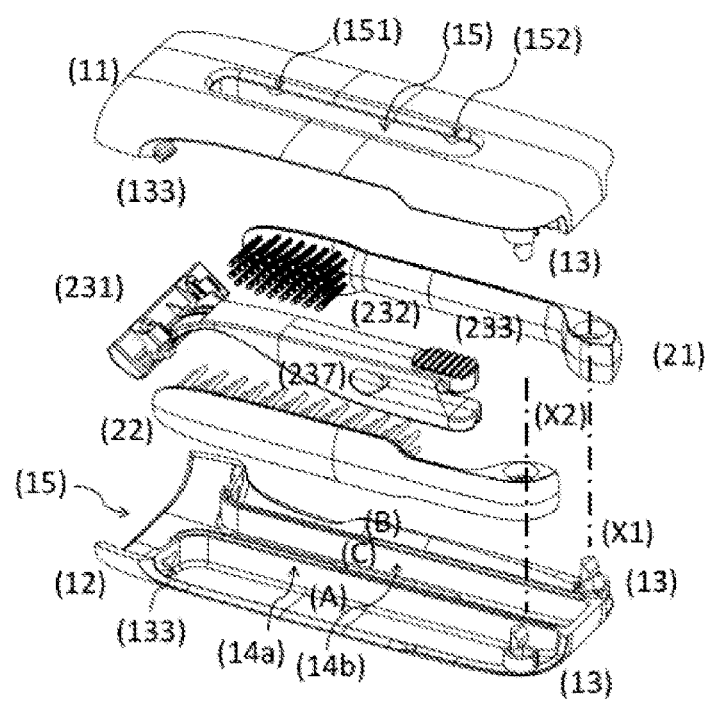
FIG. 14: shows a perspective exploded view of the embodiment according to FIG. 9, with the utensils (21, 22, 23) in closed position.
Figure 15:
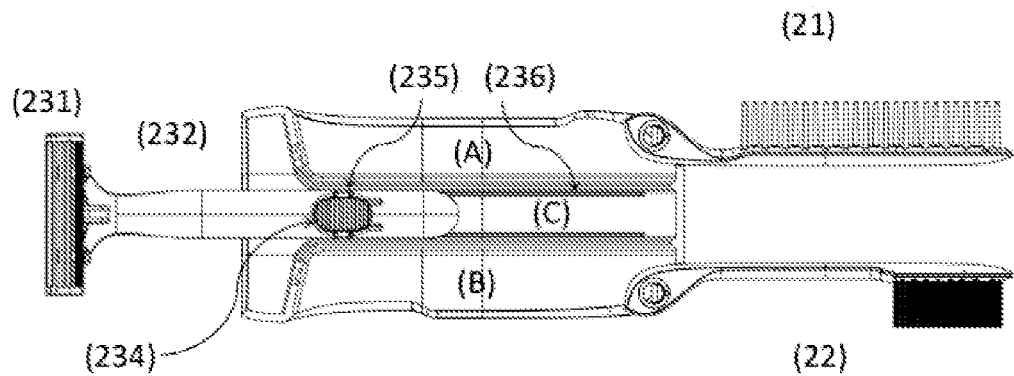
FIG. 15: shows a top view without a first casing part (11) of a particular embodiment of retention of the third utensil (23) according to FIG. 9.
Figure 16:
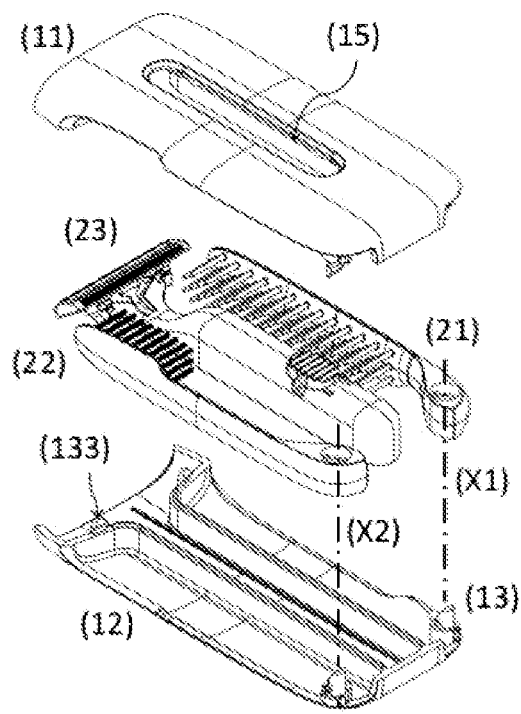
FIG. 16: shows a perspective exploded view of the embodiment according to FIG. 15, with the utensils (21, 22, 23) in closed position.
Figure 17:
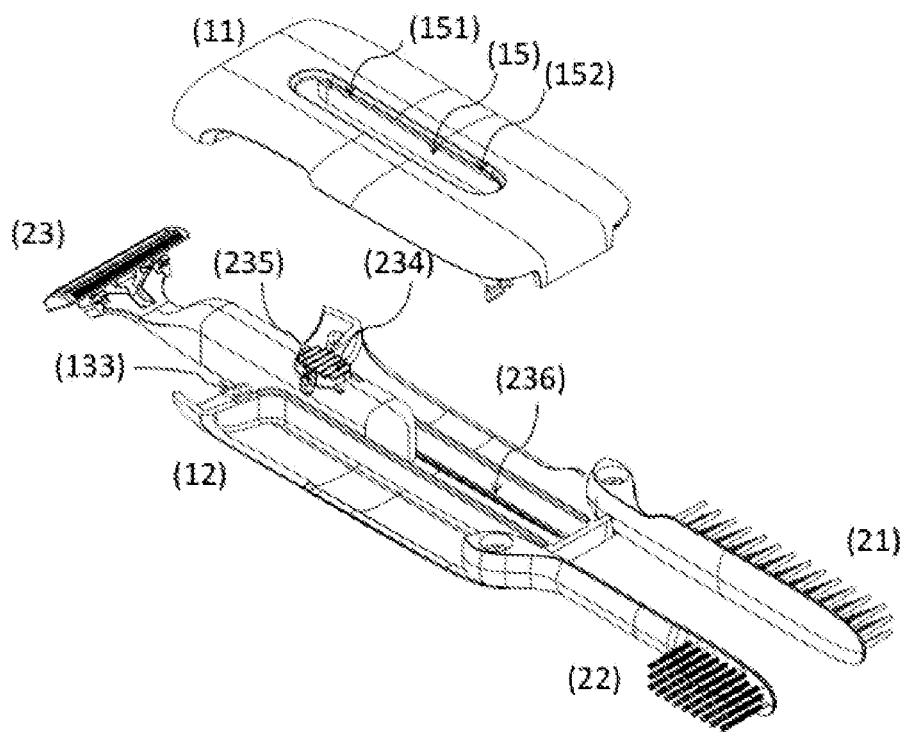
FIG. 17: shows a perspective exploded view of the embodiment according to FIG. 15, with the utensils (21, 22, 23) in open position.
Figure 18:
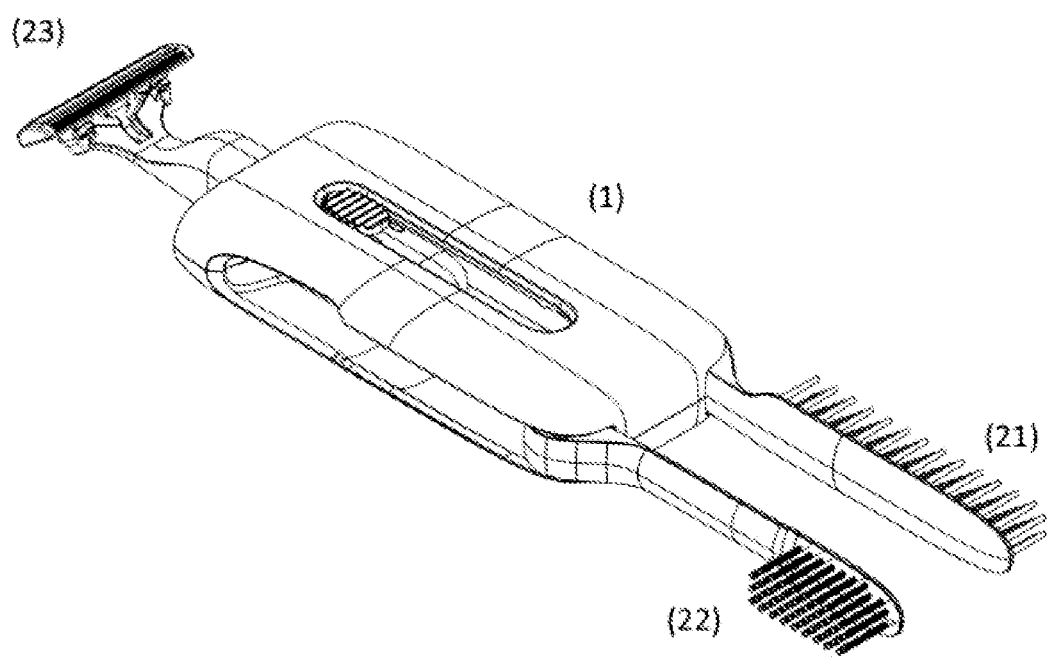
FIG. 18: shows a perspective exploded view of the embodiment according to FIG. 15, with the utensils (21, 22, 23) in open position.

As can be better observed in the details of the FIG. 6, the mechanic retention part (131) is configured with a hook shape and provided in a piece that extends in the direction towards the other casing part (11, 12) and is arranged in a reciprocally symmetric position in terms of fitting with relation to a reference central engagement axis, so that the directly opposite mechanic retention parts (131) of the casing parts (11, 12) can mechanically engage in reciprocal manner under pressure.

The support part (132) is configured with a generally tubular shape and complementary dimension, so that when the casing (1) is in the closed position and, therefore, of mutually engaged casing parts (11, 12), the support parts (132) provide a circular exterior surface disposed in centred manner with relation to a swivelling axis (X1, X2) and so that can support a connection of mobile swivelling type of a connection portion (213, 223) of the first and second utensils (21, 22).

The casing connections (13; 131, 132) in this case present a similar construction and dimension in both the casing parts (11, 12), only differing in the relative position of component parts relative to a reference central axis of engagement.

Figure 4:
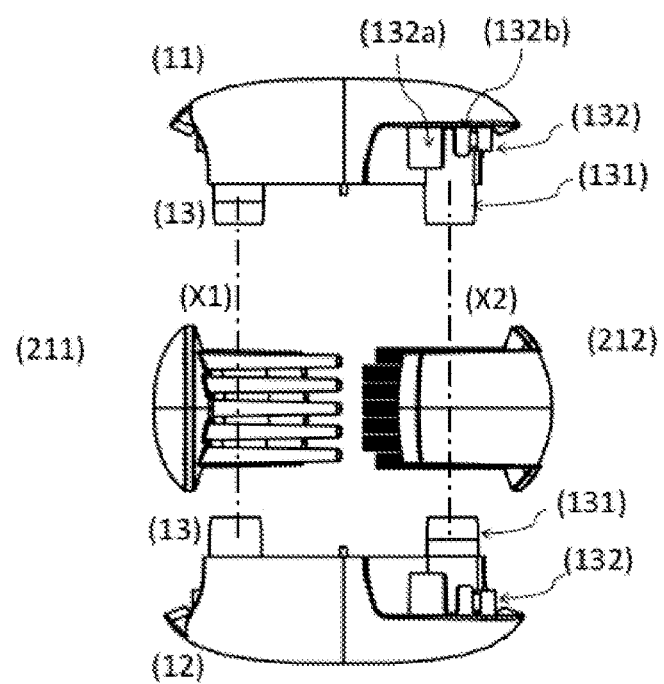
FIG. 4: shows an exploded top view of the embodiment according to FIG. 1.

Moreover, as can be better observed in FIG. 4, the support parts (132) present a first region (132a) of generally tubular shape, with a circular exterior surface in a extension that corresponds to the amplitude of the swivelling movement, for example of about 180°, and delimited on both sides by second regions (132b) adapted so that can engage in retention means (or retention unit) provided inside of support connection portions (213, 223) of the utensils (21, 22). In the case of the represented embodiment, said second regions (132b) are configured in form of cavities where can engage hard nodes (213a, 213b) provided in corresponding positions of limit of the movement on the interior surface of the support connection portions (213, 223) of first and second utensils (21, 22).

As can be better observed in the details I, II and III of FIG. 6, the connection portions (213, 223) present hard nodes (213a, 213b) disposed in opposite side of the interior surface, adapted so that can engage by means of fitting in the region of the connection parts (132).

It is herewith advantageously provided a mechanic retention of the utensils (21, 22) in respective open and closed positions, as well as a tactile perception by the user that the utensils (21, 22) are in these positions.

Moreover, the casing parts (11, 12) present respective parts of a divisor wall (14) that extends longitudinally so that divides interior collection spaces (A, B) for the hygiene utensils (21, 22), thereby separating these from each inside of the casing (1). Said parts of divisor wall (14) can present engagement means (or engagement unit), for example in the form of slot (141) and groove (142) along the respective top region, herewith providing an additional reinforcement of retaining connection of the casing parts (11, 12) along the longitudinal extension thereof.

The first and second casing parts (11, 12) present casing connections (13; 131, 132) adapted so that provide reciprocal mechanic engagement by means of a retention movement by one part in the other according to at least one of:
  along a similar direction common to the corners of the casing parts (11, 12), whereby said direction is preferentially orthogonal relative to the top face of the casing parts (11, 12) defined by the first and second extension of the casing (1);
  along a first direction in the case of two of the four corners, and along a second direction in the case of the other two corners, whereby said first and second directions are at least approximately orthogonal to each other.

The first and second casing parts (11, 12) can be provided in a synthetic material and produced as single pieces, preferentially by means of mold injection.

FIGS. 9 to 18 represent a second embodiment of the hygiene kit according to the present invention, whereby besides of the first and second utensils (21, 22) there is further provided a third of personal hygiene utensil (23), in this case in the form of a shaving blade.

As represented, the casing (1) in this case further presents a generally rectangular shape when seen from the top, maintaining the relative dimension of the first and third extension, but now with a second extension of bigger dimension relative to those.

The casing (1) further presents two utensils (21, 22) provided so that can be operated in swivel around respective swivelling axis (X1, X2), between closed and open positions, and vice-versa, without said manipulation requiring opening the casing (1). In particular, the swivelling axis (X1), X2) are further provided so that said utensils (21, 22) result with respective operative parts oriented inwards when in the closed position. However, in this case, said swivelling axis (X1, X2) are provide in corner regions on a same side of the casing (1), so that the first and second utensils (21, 22) extend on a same direction when in an open position.

Moreover, the lateral casing opening (111, 112; 121, 122) are also in this case provided so that the first and second utensils (21, 22) can be collected in respective interior spaces (A, B) of the casing (1) with respective operative portions turned face to face, instead of back to back.

In the case of this embodiment, said casing part (1) further presents a third casing opening (113) disposed on a transversal side of the casing (1) and adapted so that provides collection of at least part of a third utensil (23) in the collection space of the casing part (1) between the collection spaces of said first and second utensils (21, 22).

The casing (1) presents in this case a double interior wall (14) configured so as to confine the collection spaces of each of the utensils (21, 22, 23), in particular extending along the longitudinal direction of the casing (1), and thereby prevent eventual crossed exposure to contaminants or dirt, according to respective uses of personal hygiene.

Moreover, at least one of the first and second casing parts (11, 12) presents a manipulation opening (15) adapted so that enables the manipulation of a third utensil (23) forward and backwards along a linear extension in a respective interior collection space (C), between a position of at least partial collection inside the casing (1) and an operative position where it is distended out of the casing part (1).

In the case of this embodiment, the casing (1) further presents a third casing opening (113) adapted so that provides collection of at least part of a third utensil (23) in a third interior space (C) of the casing (1) provided between the collection spaces (A, B) of first and second utensils (21, 22).

At least one of said first and second casing parts (11, 12) presents a manipulation opening (15) provided on at least one side, preferentially on a top face thereof, and adapted so that enables the manipulation of a third utensil (23) frontwards and backwards along a linear extension, between an at least partially collection position in a third interior space of the casing part (1) and an operative position where it is distended out of the casing (1).

Said third utensil (23) presents a support part (231) that can have a characteristic dimension, in particular length, that is smaller than the length of the interior space of the casing (1), and an operative part (232) that can have a characteristic dimension, in particular width, similar to the width of the manipulation opening (15), and that extends along a transversal direction with a dimension similar to the second extension of the casing part (1).

At least said third utensil (23), preferentially also at least one of the first and second utensil (21, 22), can present an operative part (212, 222, 232) adapted so that can be manually replaced, without requiring the use of a tool for such purpose, so that there is enabled the possibility of replacement thereof at the end of a respective useful life.

The third utensil (23) further presents an actuation handle (234) provided so that projects outside of said manipulation opening (15) and configured so that can be operated by a finger of the user, preferentially one of the fingers of the hand that holds the hygiene kit.

The actuation handle (234) engages in mobile manner in the manipulation opening (15) so that can be displaced frontwards and backwards, and vice-versa, along thereof, and provides retention of the third utensil (23) so that the latter cannot exit through the collection opening (15) when moved to an open position.

The third utensil (23) presents mobile engagement means (235) provided in mutually opposing side of said actuation handle (236), and that engage with hard nodes (151, 152) provided on the inward-oriented side of a casing part (11) on both sides in the proximity of the opening (15), in limit regions of the linear movement path of actuation of the third utensil (23).

It is herewith advantageously provided retention perceptible by the user of the third utensil (23) in closed and open position.

Moreover, in the case of this embodiment, the third utensil (23) presents engagement means (236a, 236b) adapted so that can engage in mobile manner along grooves (236) provided in directly opposing side of interior walls (141) of at least one of the casing parts (11, 12), and thereby provide linear displacement frontward and backward, between collected and distended positions, and vice-versa.

The third utensil (23) can further present retention means (237) provided in the free edge opposite to the operative part (231) and adapted so that can be retained in a part of the third interior space (C) of the casing (1). In the case of this embodiment, said retention means (237) are provided in the form of an elastic clip of spring type.

FIGS. 15 to 18 represent a variant of retention of the third utensil (23).

The casing parts (11, 12) in this case present connection parts (13) adapted so that provide reciprocal retention along a movement in a single direction of approach and reciprocal engagement. In particular, beyond two first connection parts (131, 132) provided in corner regions on a same side of the casing (1), the casing parts (11, 12) present two second connection parts (133) provided in diametrically opposite corner regions of the casing (1), in particular longitudinally opposite, and configured for example as engagement hooks by reciprocal engagement.

The third utensil (23) further presents an actuation handle (234) provided so that projects out of said manipulation opening (15), as well as mobile engagement means (235) provided in mutually opposite sides of said actuation handle (236), and that engage with hard nodes (151, 152) of the casing part (11) that presents the manipulation opening (15).

But, in the case of this embodiment, the third utensil (23) is configured with a support part (232) of dimension and shape at least approximately similar to the third collection space (C), so that can be collected therein and in form of mobile engagement along the longitudinal direction of the casing (1). Moreover, the third utensil (23) presents mobile engagement means (not represented in the drawing) associated with the opposite side of the third utensil (23) and configured so that engage in mobile manner in respective sliding guides (236) provided on the other casing parts (12) and herewith provide a sliding of the third utensil (23) between closed and open positions, and vice-versa.

It is herewith provided a third utensil (23) with a simpler form.

Moreover, a replacement of the third utensil (23) can be carried out in analogous manner to the first and second utensil (21, 22), sufficing that the user removes a first casing part (11), removes an old utensil (21, 22, 23) and places a new one, by means of a similar gesture in all cases, along a direction orthogonal to the longitudinal direction of the casing (1).

The third utensil (23) can be provided so that can be removed from the casing (1) for use thereof, and be retained back again inside the casing (1) after such use.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. Hygiene kit, comprising:
a casing comprising a first and a second casing part, each configured with a general handle-like handle grip, elongated along a longitudinal direction, and adapted to be retained with each other and thereby provide an interior space of the casing,
a first and a second personal hygiene utensil comprising a support part and an operative part,
wherein said first and second utensils are provided so that they can be operated in respective swiveling axes between open positions where they can be used, and closed positions where they can be collected through opposite sides inside the interior space of the casing, without requiring opening the casing, wherein the first and second casing parts comprise a plurality of casing connections adapted to be reciprocally retained in a mechanical manner, and to be manually removed from retention without requiring the use of a tool, wherein the first and second casing parts are each provided as a single piece, including all casing connections, so that the hygiene kit does not include any part besides the casing parts and the hygiene utensils, and wherein said casing connections are further adapted so that they can also operate as a support beam for a swiveling connection of the support beam with connection portions of the first and second utensils, said casing part further comprises a third casing opening adapted to provide collection of at least part of a third utensil in a third interior collection space of the casing between first and second interior collection spaces for the first and second utensils, and at least one of the first and second casing parts comprises a manipulation opening provided on at least one side, on a top face thereof, and adapted to enable a manipulation of the third utensil forward and backward along a linear extension between an at least partially collected position in the third interior collection space and an operative position where it is distended out of the casing.

2. Hygiene kit according to claim 1, wherein when the first and second utensils are in the closed position, their operative parts are collected in respective first and second interior spaces of the casing through a casing side opening configured in at least one of the casing parts and with the operative parts extending inwards, and wherein when the first and second utensils are in the open position, at least the support parts, and also the operative parts, extend along a direction parallel to longitudinal lateral regions of the casing, and along at least one of:

opposite directions,
similar directions, so that the functional portions of the operative parts are oriented in opposite directions, both directed outwards and along a longitudinal direction with relation to the casing.

3. Hygiene kit according to claim 1, wherein at least one of, or both of, the first and second casing parts are provided with a configuration of a half-shell type and configure first and second interior spaces accessible through side casing openings in mutually opposing lateral regions and extending along a first longitudinal extension of the casing, and the first and second utensils comprise a dimension adapted so that they can be associated with swiveling axis disposed at least in the proximity of a corner region of the casing, and wherein they extend along at least part, or of the most part of a first longitudinal extension of the casing, wherein they can be collected in mutually opposing lateral regions that extend along a first longitudinal extension of the casing.

4. Hygiene kit according to claim 1, wherein the first and second casing parts comprise casing connections configured in pairs in each casing part and so that they provide a reciprocal engagement with each other of mechanic clipping type or bayonet-like connection, of the first and second casing parts, and the edge region of the support part of the first and second utensils comprises a support connecting portion adapted to be retained in a corresponding casing connection of the casing part, wherein said casing connection is adapted to provide swiveling of the first and second utensils between respective closed and open positions, and vice-versa.

5. Hygiene kit according to claim 1, wherein the first and second casing parts comprise two first casing connections adapted to provide reciprocal retention and swiveling support to the first and second utensils, wherein said first casing connections are configured as reciprocal pressured fitting connections, and an end region of the support parts of the first and second utensils opposite to the operative parts comprises a connection portion that comprises a portion configured to be rotated between closed and open positions, and that surrounds at least partially a portion of a circular shape that can operate as a female part in a swiveling connection to a first casing connection provided in the casing.

6. Hygiene kit according to claim 1, wherein the first and second casing parts comprise two or four casing connections including two first casing connections and two second casing connections, and the first and second casing parts comprise casing connections that can be at least one of:

a pair of similar configurations in both of the casing parts, including a reciprocally retaining hook type;
a pair of different configurations in each casing part, including a male-female type.

7. Hygiene kit according to claim 1, wherein the first and second casing parts comprise first casing connections that comprise a reciprocal mechanic retention part and a tool support part that extends in tubular manner, around the mechanic retention part, and in a centered manner with relation to the swiveling axis, with a characteristic dimension, in particular an exterior diameter, smaller by a swiveling tolerance than a characteristic dimension, in particular an interior diameter, provided in connection parts on the edges of the first and second utensils, and the first and second casing parts comprise first casing connections disposed in at least two corner regions of opposite sides of the casing, wherein the swiveling axes of the first and second utensils are provided in diametrically opposing corner regions of the casing, or in corner regions of a same side of the casing.

8. Hygiene kit according to claim 1, wherein said third tool comprises a support part that presents a characteristic dimension, smaller than a length of the interior space in the casing, and an operative part that presents a characteristic dimension, including a width, at least approximately equal to a width of the third manipulation opening, and that extends along a transversal direction with a dimension at least approximately equal to the second extension of the casing part, and at least said third utensil, and at least one of the first and second utensils, comprises an operative part adapted to be manually replaced.

9. Hygiene kit according to claim 1, wherein the third utensil further comprises an actuation handle provided to project outside of the manipulation opening and configured to be operated by a finger of the user or one of the fingers of the hand that holds the hygiene kit, and the third utensil comprises a mobile engagement unit provided in mutually opposing sides of the respective support part of the actuation handle, and adapted to engage in a mobile manner along grooves provided in directly opposite sides of interior walls of at least one of the casing parts, and thereby provide a linear displacement frontwards and backwards, between collected and distend positions, and vice-versa.

10. Hygiene kit according to claim 1, wherein
said third utensil further comprises a retention unit provided in a free edge opposite to the operative part and adapted so that it can be retained in a part of the third interior space of the casing.

11. Hygiene kit according to claim 1, wherein
the casing part comprises a generally parallelepiped shape with a first extension along a first longitudinal direction, a second extension in a direction transversal to the first direction and a dimension smaller than that of the first extension, and a third extension in a direction transversal to the first and second directions and a dimension smaller than the second extension, wherein said casing openings are configured along the first and third extension, and wherein the casing part is configured with the shape of a handle that can be held by a single hand and does not comprise at least one of:
   a configuration of an elongated type wherein the most part of the lateral extensions, when the casing is seen sideways, is occupied by the lateral casing openings of the first and second utensils, and
   a configuration comprising at least two corners of a rounded shape, when the casing is seen in top view, and provided by edge regions of the first and second utensils.

12. Hygiene kit according to claim 1, wherein
the first and second casing parts are adapted so that, when they are assembled together and none of the utensils is in an open position, they provide a piece with a substantially continuous surface devoid of openings, and at least one of the casing parts comprises at least one of:
   an interior wall configured so that it provides separation of collection spaces of the first and second utensils, and
   two interior walls configured so that they delimit a collection space of said third utensil in-between them, and so that they provide a separation relative to collection spaces of the first and second utensils.

13. Hygiene kit according to claim 1, wherein
said swiveling axes are provided in two corner regions of the casing, and arranged to extend along a direction transversal to the frontal faces of the first and second casing parts that extend between side faces that comprise casing side openings, and wherein said swiveling axes are disposed in at least one of:
   in diametrically opposing corner regions, that is, on opposite sides of the casing, including in opposite side defined by a first and second extension of the casing, and
   in both of the corner regions on a same side of the casing, including on the corners defined by a first and second extension of the casing.

* * * * *